US012608807B2

(12) United States Patent
Grimm et al.

(10) Patent No.: US 12,608,807 B2
(45) Date of Patent: Apr. 21, 2026

(54) METHOD OF GENERATING A METRIC TO QUANTITATIVELY REPRESENT AN EFFECT OF A TREATMENT

(71) Applicant: HOFFMANN-LA ROCHE INC., Little Falls, NJ (US)

(72) Inventors: Oliver Grimm, Basel (CH); Marta Canamero, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 494 days.

(21) Appl. No.: 18/155,699

(22) Filed: Jan. 17, 2023

(65) Prior Publication Data

US 2023/0177691 A1 Jun. 8, 2023

Related U.S. Application Data

(63) Continuation of application No. PCT/EP2021/064063, filed on May 26, 2021.

(30) Foreign Application Priority Data

Jul. 21, 2020 (EP) .................................... 20186928

(51) Int. Cl.
*G06T 7/00* (2017.01)
*G06T 7/11* (2017.01)
*G16H 50/30* (2018.01)

(52) U.S. Cl.
CPC .............. *G06T 7/0016* (2013.01); *G06T 7/11* (2017.01); *G16H 50/30* (2018.01);
(Continued)

(58) Field of Classification Search
CPC ......... G16H 50/30; G06T 7/0016; G06T 7/11; G06T 2207/10056; G06T 2207/20021;
(Continued)

(56) References Cited

U.S. PATENT DOCUMENTS 7,492,931 B2 2/2009 Sabol et al.
10,638,948 B2 * 5/2020 Gazit ................... A61B 5/7282
(Continued)

FOREIGN PATENT DOCUMENTS

EP 3155592 B1 9/2019
WO 200198774 A2 12/2001
(Continued)

OTHER PUBLICATIONS

Glaister Jeffrey et al: "Segmentation of Skin Lesions From Digital Images Using Joint Statistical Texture Distinctiveness", IEEE Transactions on Biomedical Engineering, IEEE Service Center, Piscataway, NJ, USA, vol. 61, No. 4, Apr. 1, 2014.
(Continued)

*Primary Examiner* — Katrina R Fujita
(74) *Attorney, Agent, or Firm* — Harness, Dickey & Pierce, P.L.C.

(57) ABSTRACT

Methods of generating a metric to quantitatively represent an effect of a treatment are disclosed. In one arrangement, first and second sample data units are received, each representing a segmented image of a biological sample taken from a subject. The segmentation divides the image into plural segmentation sets of regions. Each of the first and second sample data units is analysed to determine information about a spatial distribution of biomarkers relative to the segmentation sets. A metric is generated using a combination of the determined information about the spatial distribution of biomarkers relative to the segmentation sets for the first and second sample data units.

17 Claims, 5 Drawing Sheets

(52) U.S. Cl.
CPC .............. *G06T 2207/20021* (2013.01); *G06T*
*2207/30096* (2013.01); *G06T 2207/30204*
(2013.01)

(58) Field of Classification Search
CPC . G06T 2207/30092; G06T 2207/30096; G06T
2207/20204; G06T 2207/30204
See application file for complete search history.

(56) References Cited

U.S. PATENT DOCUMENTS

| | | | | |
|---|---|---|---|---|
| 11,881,311 | B1 * | 1/2024 | Fortney | G16H 50/30 |
| 2008/0219529 | A1 * | 9/2008 | Alexandrov | G06V 10/771 |
| | | | | 382/128 |
| 2010/0216247 | A1 * | 8/2010 | Bose | G01N 33/57434 |
| | | | | 436/63 |
| 2012/0147010 | A1 * | 6/2012 | Schmidt | G06T 11/206 |
| | | | | 345/440 |
| 2013/0080134 | A1 * | 3/2013 | Donovan | G16H 50/50 |
| | | | | 703/11 |
| 2013/0329973 | A1 | 12/2013 | Cao et al. | |
| 2014/0161342 | A1 * | 6/2014 | Schauer | B65D 85/76 |
| | | | | 382/133 |
| 2015/0293026 | A1 * | 10/2015 | Shin | G06V 20/693 |
| | | | | 435/7.1 |

| | | | | |
|---|---|---|---|---|
| 2017/0135615 | A1 * | 5/2017 | Hasan | A61B 5/14551 |
| 2019/0183796 | A1 | 6/2019 | Egan et al. | |
| 2019/0287240 | A1 * | 9/2019 | Gaire | G06T 7/0012 |
| 2020/0321102 | A1 * | 10/2020 | Barnes | G06V 20/695 |
| 2021/0166406 | A1 * | 6/2021 | Sperl | G06T 7/337 |
| 2023/0033034 | A1 * | 2/2023 | Tai | G06T 7/0016 |
| 2023/0176064 | A1 * | 6/2023 | Lee | G01N 33/542 |
| | | | | 435/7.1 |
| 2023/0360217 | A1 * | 11/2023 | Wang | G06T 7/40 |

FOREIGN PATENT DOCUMENTS

| | | | | |
|---|---|---|---|---|
| WO | 2016120441 | A2 | 8/2016 | |
| WO | WO-2017198790 | A1 * | 11/2017 | G06T 7/0012 |
| WO | 201802385 | A1 | 1/2018 | |
| WO | 202072348 | A1 | 4/2020 | |

OTHER PUBLICATIONS

International Serarch Report and Written Opinion regarding International Patent Application No. PCT/EP2021/064063, dated Dec. 8, 2021.
T. L. Jones et al: "Brain tumor classification using the diffusion tensor image segmentation (D-SEG) technique", Neuro-Oncology, Aug. 13, 2014.

* cited by examiner

Fig. 4

METHOD OF GENERATING A METRIC TO QUANTITATIVELY REPRESENT AN EFFECT OF A TREATMENT

CROSS REFERENCE TO RELATED APPLICATIONS

This application is a U.S. Continuation Application of International Application No. PCT/EP2021/064063, filed on May 26, 2021, which claims priority to European Patent Application No. 20186928.6, filed on Jul. 21, 2020. The entire disclosures of the above applications are expressly incorporated by reference herein.

The present disclosure relates to generating a metric to quantitatively represent an effect of a treatment.

Assessing the effect of a candidate treatment for a condition or disease is an important part of the drug development process. Visually recognisable biomarkers can provide information about the effect of a treatment, but interpretation of the relevant images can be difficult or unreliable. In some cases, complex data processing procedures are needed to transform the images to a form that can be readily interpreted. Time-consuming training may be needed to enable assessors to interpret images in a consistent way. Even with data processing and training it is difficult to avoid subjectivity and/or inconsistency in interpretations.

It is an object of the invention to provide an approach for assessing the effect of a treatment that can be applied efficiently and reliably without requiring excessive computational resource or training on the part of assessors and/or which is capable of extracting more information from the measurements being performed.

According to an aspect of the invention, there is provided a computer-implemented method of generating a metric to quantitatively represent an effect of a treatment, the method comprising: receiving a first sample data unit derived from a subject before a treatment has been applied and receiving a second sample data unit derived from the subject after the treatment has been applied, or receiving a first sample data unit derived from a subject after a first treatment has been applied to the subject and receiving a second sample data unit derived from the subject after a second treatment has been applied to the subject, the second treatment being different from the first treatment; and wherein each of the sample data units represents a segmented image of a biological sample taken from the subject, the segmentation dividing the image into plural segmentation sets of regions, each segmentation set representing regions in the image that correspond to a different respective tissue type; and wherein the method further comprises: analysing each of the first sample data unit and the second sample data unit to determine information about a spatial distribution of biomarkers relative to the segmentation sets; and generating a metric using a combination of the determined information about the spatial distribution of biomarkers relative to the segmentation sets for the first sample data unit and the second sample data unit.

The inventor has found that the above approach to generating a metric can be implemented using minimal computational resources. Furthermore, metrics output by the method have been shown to be easily interpretable by a user and to efficiently encapsulate relevant information about the effect of the treatment being investigated. The method provides an improved balance of efficiency of implementation relative to metric performance.

In one class of embodiment, the information about the spatial distribution of biomarkers relative to the segmentation sets comprises:

first information, comprising information about the spatial distribution of biomarkers in a first one of the segmentation sets; and second information, comprising information about the spatial distribution of biomarkers in a second one of the segmentation sets. The metric may be generated using the first and second information for the first sample data unit and the first and second information for the second sample data unit. The generation of the metric may comprise obtaining a vector having end points defined by the first and second information for the first sample data unit and the first and second information for the second sample data unit.

The inventors have found that generating a vector in this way provides the foundation for a range of metrics that can efficiently convey information about the effect of the treatment that has been derived from the available sample data units. The magnitudes and arguments (or slopes) of the generated vectors can provide independent information about the effect of the treatment, as well as each providing an efficient summary of complex data in a single meaningful metric. Both the individual argument/slope and the population/cohort average argument/slope are of importance to understand/help interpret efficacy and safety events. Embodiments involving vectors are exemplified with two-dimensional vectors but the approach may be extended to vectors having more than two dimensions, such as 3 dimensions, 4 dimensions, or more.

In an embodiment, the method further comprises using the calculated arguments or slopes and/or magnitudes for plural different subjects, together with information about clinical efficacy and/or safety of an applied treatment, as input to a machine learning algorithm to build a predictive model. This approach allows reliable information to be extracted from subtle features of the generated vectors which may not be easily and/or reliably evaluated by visual inspection of a graphical representation of the generated vectors.

In an embodiment, for at least one of the segmentation sets the segmentation set comprises plural regions of the image and the information about the spatial density of the biomarkers comprises region-specific information about the spatial density of the biomarkers in each of two or more of the regions. The generation of the metric may then comprise generating a metric representing a distribution of the spatial density of the biomarkers over the two or more of the regions, optionally in the form of a histogram. This approach enables a researcher to identify differences in a homogeneity of biomarker density distributions, which further contributes information relevant to predicting or evaluating efficacy/safety of a treatment.

In some embodiments, the method comprises generating a visual representation of the metric by displaying at least the end points of the vector on a graph. This visual display allows the information contained in the generated metric to be conveyed efficiently to a user. Metrics generated for different subjects can be easily compared.

The inventor has shown that the approach of embodiments of the disclosure is particularly effective in the context of assessing the effects of immunotherapy drugs and/or treatments that depend on the efficiency with which immune cells infiltrate particular tissue types, such as tumor nest tissue.

Embodiments of the disclosure will be further described by way of example only with reference to the accompanying drawings, in which:

FIG. 4 depicts a plot of CD8+ cell densities in tumor nests versus CD8+ cell densities in stroma for baseline samples (before treatment) and on-treatment samples.

Embodiments of the disclosure relate to computer-implemented methods of generating a metric representing the effect of a treatment. Methods of the present disclosure are thus computer-implemented. Each step of the disclosed methods may be performed by a computer in the most general sense of the term, meaning any device capable of performing the data processing steps of the method, including dedicated digital circuits. The computer may comprise various combinations of computer hardware, including for example CPUs, RAM, SSDs, motherboards, network connections, firmware, software, and/or other elements known in the art that allow the computer hardware to perform the required computing operations. The required computing operations may be defined by one or more computer programs. The one or more computer programs may be provided in the form of media or data carriers, optionally non-transitory media, storing computer readable instructions. When the computer readable instructions are read by the computer, the computer performs the required method steps. The computer may consist of a self-contained unit, such as a general-purpose desktop computer, laptop, tablet, mobile telephone, or other smart device. Alternatively, the computer may consist of a distributed computing system having plural different computers connected to each other via a network such as the internet or an intranet.

Figure 1:
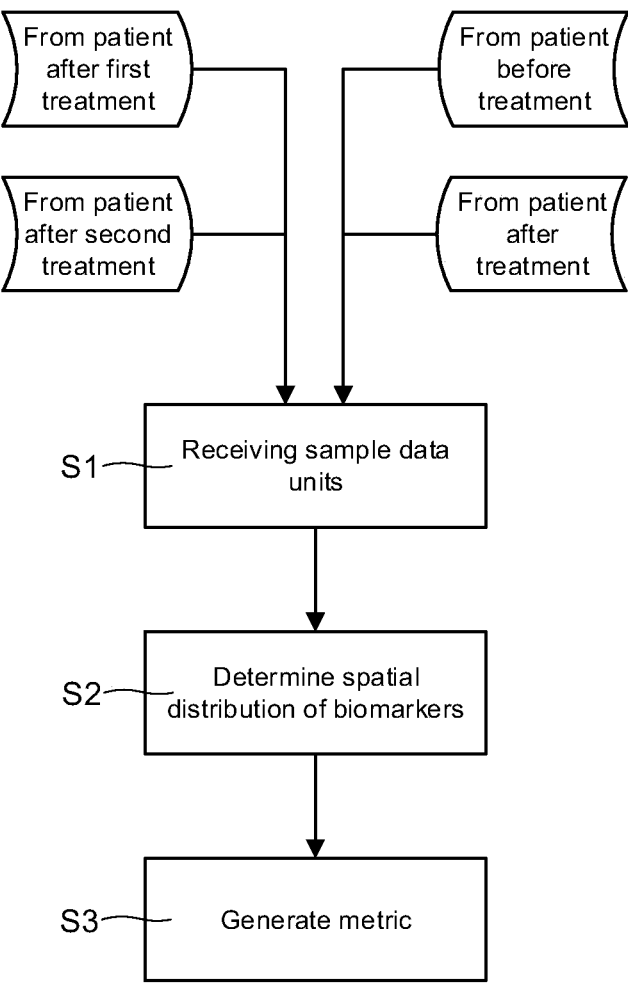
FIG. 1 is a flow chart showing a framework for methods of generating a metric to represent the effect of a treatment.

FIG. 1 is a flow chart showing a schematic framework for methods of the disclosure. The methods generate a metric (e.g. a scalar number, vector, or graph). The metric quantitatively represents an effect of a treatment.

Step S1 of the method comprises receiving a first sample data unit and a second sample data unit. In one class of embodiment, the first sample data unit is derived from a subject (e.g. a human patient) before a treatment has been applied to the subject and the second sample data unit is derived from the subject after the treatment has been applied. In another class of embodiment, the first sample data unit is derived from a subject after a first treatment has been applied to the subject and the second sample data unit is derived from the subject after a second treatment has been applied to the subject. The second treatment is different from the first treatment. For example, the first and second treatments may involve treatments based on different drugs and/or different dosage regimes. In some embodiments, either or both of the treatments comprises application of an immunotherapy drug, but the general approach is applicable to other therapies.

Each of the sample data units represents a segmented image of a biological sample taken from the subject. The segmentation may involve dividing the image into plural segmentation sets of regions. Each segmentation set represents regions in the image that correspond to a different respective tissue type. Any of various known approaches to image segmentation according to tissue type may be used. The segmentation may be performed automatically (using an automated segmentation algorithm), manually (e.g. expert-provided), or by a combination of the two.

Figure 2:
FIG. 2 depicts an image with annotations indicating locations of tumor nest and detected CD8+ cells.
Figure 3:
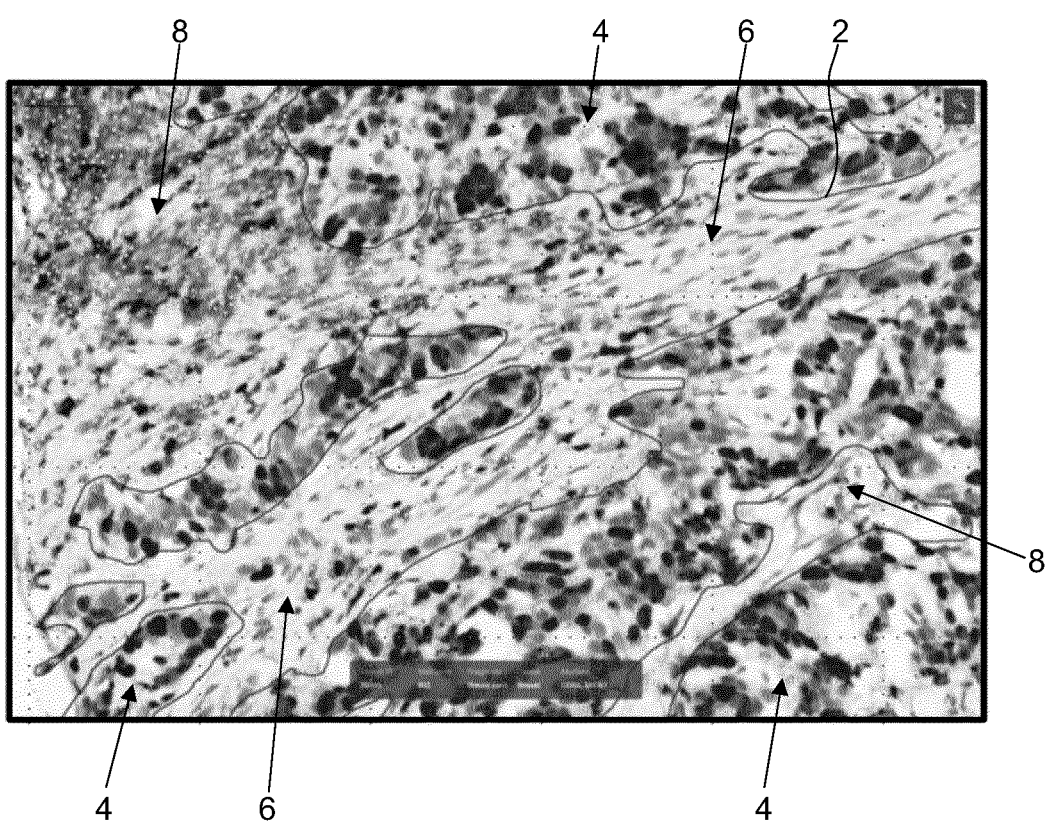
FIG. 3 depicts a magnified field of view of the image of FIG. 2.

FIGS. 2 and 3 depict examples of segmented images of a biological sample. In this example, the biological sample comprised a tissue section with CD8+ cells stained via immunohistochemistry (IHC). The method is not limited to using stained CD8+ cells. Any other biomarker suitable for indicating an effect of a treatment may be used. FIG. 2 is an image of a whole slide showing tumor nest annotations as dark grey closed loops 2 (for practical illustration purposes, only a small representative portion of the tumor nest annotations are indicated by the reference number "2"). Each loop 2 surrounds are region 4 of the image that is thought to predominantly or exclusively contain tumor nest (sometimes referred to as cancer nest) tissue. FIG. 3 is a magnified field of view of the image of FIG. 2, in which stained CD8+ cells 8 are visible as well as the segmentation indicated by the tumor nest annotations (loops 2) (for practical illustration purposes, only a small representative portion of the stained CD8+ cells are indicated by the reference number "8").

The set of regions 4 surrounded by the loops 2 is thus an example of a segmentation set of regions. Each region 4 in the segmentation set corresponds to tumor nest tissue. The set of regions 6 outside of the loops 2 is a further example of a segmentation set of regions, in this case corresponding to stroma tissue.

Step S2 of the method comprises analysing each of the first sample data unit and the second sample data unit to determine information about a spatial distribution of biomarkers relative to the segmentation sets. The nature of the biomarker is not particularly limited. In some embodiments, the biomarker comprises a stained cell. The biomarker may comprise an immune cell, preferably a cytotoxic T cell as in the example discussed with reference to FIGS. 2 and 3. The determination of the information about a spatial distribution of biomarkers may comprise detecting the position of each of at least a subset of the biomarkers in the image. This detection may be performed automatically (i.e. by a computer) or manually. In the example described with reference to FIGS. 2 and 3, pale circular points indicate detected locations for each of the stained CD8+ cells. In some embodiments, the information about the spatial distribution of biomarkers relative to the segmentation sets comprises information about a spatial density of the biomarkers (e.g. the number of biomarkers per unit area) in each of one or more of the segmentation sets. In the example of FIGS. 2 and 3, the information about spatial distribution of biomarkers may comprise the number of stained CD8+ cells per unit area in the segmentation set corresponding to tumor nest tissue and, separately, the number of stained CD8+ cells per unit area in the segmentation set corresponding to stroma tissue. In some embodiments, the information about the spatial density of the biomarkers may be more granular. For example, where a segmentation set comprises plural regions of the image, the information about the spatial density of the biomarkers may comprise region-specific information about the spatial density of the biomarkers in each of two or more of the regions, such as within each of two or more different tumor nest regions.

Step S3 of the method comprises generating a metric using a combination of the determined information about the spatial distribution of biomarkers relative to the segmentation sets for the first sample data unit and the second sample data unit (i.e. the determined information for the first sample data unit is used in combination with the determined information for the second sample data unit).

In some embodiments, as exemplified in FIGS. 2 and 3, the information about the spatial distribution of biomarkers relative to the segmentation sets comprises first information and second information. The first information comprises information about the spatial distribution of biomarkers in a first one of the segmentation sets (e.g. an average spatial density of stained cells in the segmentation set corresponding to tumor nest tissue). The second information comprises information about the spatial distribution of biomarkers in a second one of the segmentation sets (e.g. an average spatial density of stained cells in the segmentation set corresponding to stroma tissue). In embodiments of this type, the generation of the metric in step S3 may be performed using the first and second information for the first sample data unit (e.g. for a patient before treatment or after a first treatment) and the first and second information for the second sample data unit (e.g. for a patient after a treatment or after a second treatment different from a first treatment). In cases where region-specific information about the spatial density of biomarkers is obtained for multiple different regions within the same segmentation set (e.g. for multiple different tumor nest regions), the generation of the metric may comprise generating a metric representing a distribution of the spatial density of the biomarkers over the multiple regions, optionally in the form of a histogram (e.g. with a height of each bar of the histogram representing a spatial density of biomarkers in a respective region).

Figure 4:
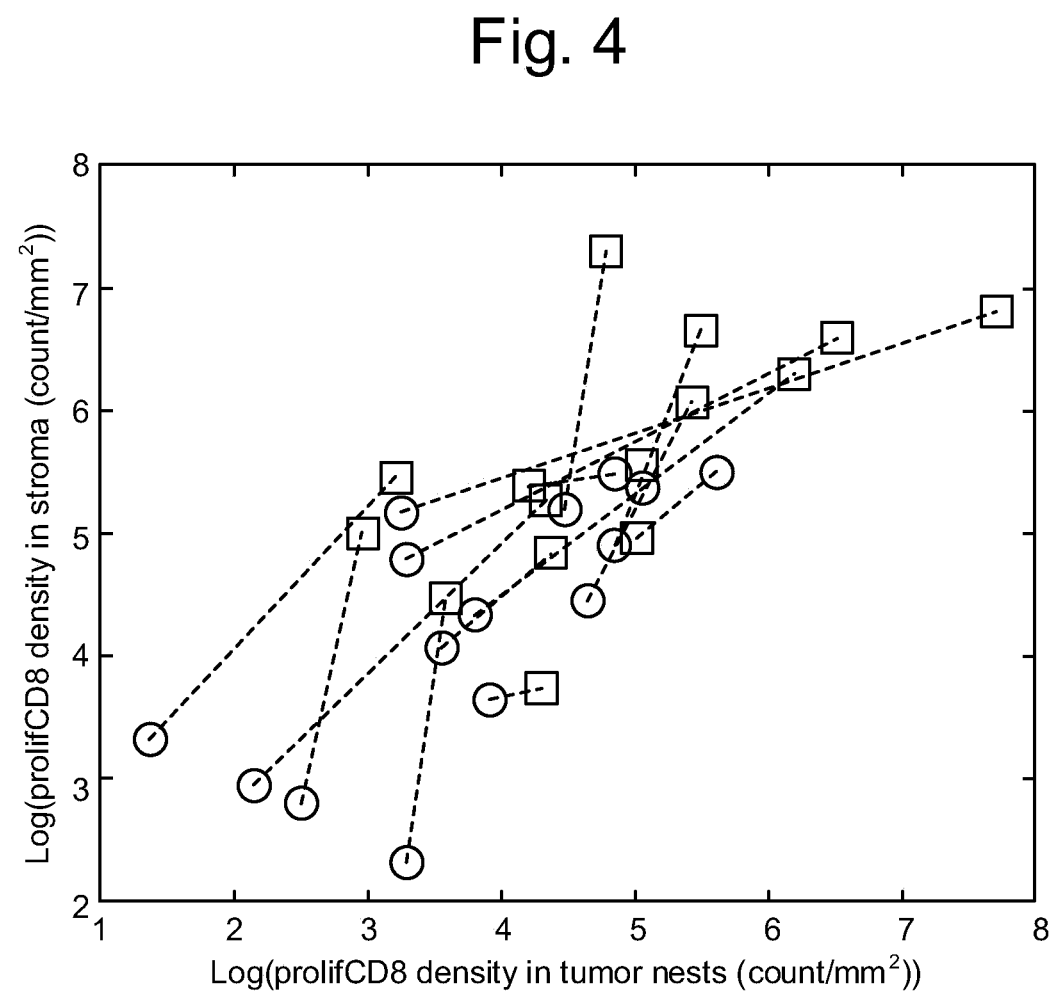
Figure 5:
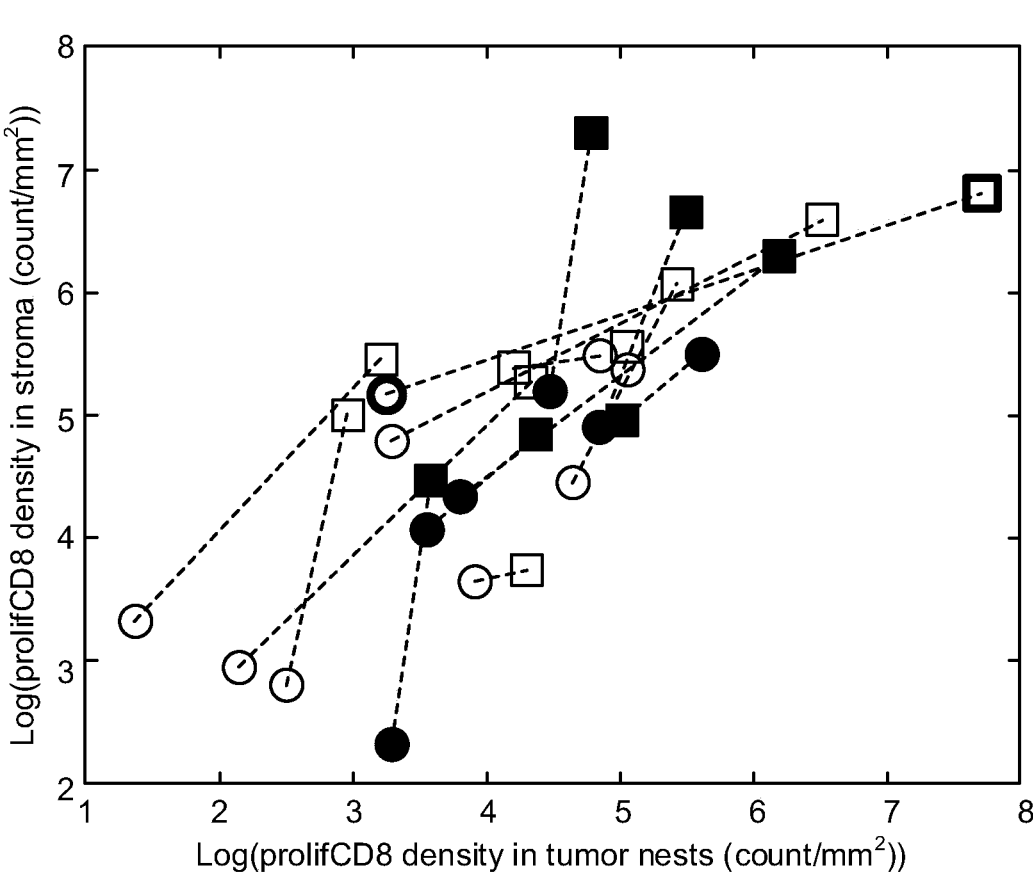
FIG. 5 depicts the plot of FIG. 4 with a point symbol format altered to indicate further information about the samples.

In some embodiments, the generation of the metric comprises obtaining a vector having end points defined by the first and second information for the first sample data unit and the first and second information for the second sample data unit. A visual representation of the metric may be generated, as exemplified in FIGS. 4 and 5, by displaying at least the end points of the vector on a graph. FIGS. 4 and 5 depict a visual representation derived from segmented images of the type discussed above with reference to FIGS. 2 and 3, but the approach may be extended to segmented images involving other combinations of tissue types. In embodiments of this type, one axis of the graph may represent a range of possible values of the first information, while the other axis represents a range of possible values of the second information. As exemplified in FIGS. 4 and 5, a line (e.g. a broken line) may additionally be depicted that connects the end points together. This line may help the argument or slope of the vector to be distinguished more efficiently by a user. Additionally or alternatively, the line may assist with distinguishing between different metrics plotted on the same graph.

FIG. 4 depicts a plot of average CD8+ cell densities in a segmentation set corresponding to tumor nest tissue (first information) versus average CD8+ cell densities in a segmentation set corresponding to stroma tissue (second information) for a cohort of patients undergoing the same treatment. Each of the open circle points represents first and second information from a first sample data unit from a different patient. In this example, the first sample data unit was obtained before the patient had received any treatment. The open square points represent first and second information from a respective second sample data units for each patient. In this example, the second sample data unit was obtained from the patient after he or she had received the treatment under investigation. Points corresponding to the same patient are linked together visually by a broken line. The open circles and squares are thus respective end points of a vector. The metric being generated may consist of or comprise the vector or the vector may be used to generate the metric. In some embodiments, for example, the generation of the metric comprises calculating an argument or slope of the vector.

In the example shown in FIG. 4, the treatment is clearly seen to cause a marked shift towards the right/upper-right in the plotted positions of the points representing the first and second information. This shift provides a quantitative measure of the effect of the treatment, in this case providing useful information about a mode of action of a drug that causes infiltration of the tumor nest tissue by immune cells. In almost all cases, the treatment is seen to increase an average spatial density of immune cells in both the stroma and tumor nest tissue. A magnitude of the vector provides a quantitative measure of a degree to which the treatment increases the number of the immune cells generally present in the region of the tumor. An argument of the vector (counterclockwise angle relative to the positive x-axis) provides a quantitative measure of the extent to which the treatment is effective in causing immune cells to infiltrate the tumor nest tissue relative to the surrounding stroma tissue. An argument near 0 degrees indicates a strong preference for infiltration into tumor nest tissue relative to stroma tissue. An argument of 45 degrees indicates an equal tendency for infiltration into tumor nest and stroma regions. An argument near 90 degrees indicates a strong preference for infiltration into stroma tissue relative to tumor nest tissue (normally a less favourable result). Plotting vectors for different patients on the same graph allows a meaningful comparison to be made quickly and efficiently between the effect of the treatment on the different patients. In the present example, it can be appreciated immediately for example that the general effect of the treatment is to increase the spatial density of immune cells in both the stroma and tumor nest tissues. While a slight preference for infiltration into stroma tissue over the cohort may be observed, this does not appear to be a strong effect, with all but one of the patients seeing an increase in density of immune cells in the tumor nest tissue after the treatment has started.

In some embodiments, further information may be indicated on the plot. For example, classifications of the patients may be indicated. FIG. 5 depicts an example of this approach in which the patients are classified according to whether they have progressive disease, stable disease, or a partial response. Data points corresponding to patients having progressive disease are shown as open circles and squares. Data points corresponding to patients having stable disease are shown as filled circles and squares. Data points corresponding to patients having partial response are shown as bold circles and squares.

In some embodiments, metrics generated in step S3 (e.g. a calculated argument or slope and/or magnitude of a generated vector) for plural different subjects may be used together with information about clinical efficacy and/or safety of an applied treatment as input to a machine learning algorithm to build a predictive model. The predictive model may then be used to generate a new metric quantitatively representing an effect of a treatment for a new first and second sample data unit received from a patient. This approach may be used to screen patients to determine whether a particular treatment would be effective and/or safe for that patient.

The invention claimed is:

1. A computer-implemented method of generating a metric to quantitatively represent an effect of a treatment, the method comprising:

receiving a first sample data unit derived from a subject before a treatment has been applied and receiving a second sample data unit derived from the subject after the treatment has been applied, or receiving a first sample data unit derived from a subject after a first treatment has been applied to the subject and receiving a second sample data unit derived from the subject after a second treatment has been applied to the subject, the second treatment being different from the first treatment; and wherein each of the sample data units represents a segmented image of a biological sample taken from the subject, the segmentation dividing the image into plural segmentation sets of regions, each segmentation set representing regions in the image that correspond to a different respective tissue type; and wherein the method further comprises:

analysing each of the first sample data unit and the second sample data unit to determine information about a spatial distribution of biomarkers relative to the segmentation sets; and generating a metric using a combination of the determined information about the spatial distribution of biomarkers relative to the segmentation sets for the first sample data unit and the second sample data unit, wherein the information about the spatial distribution of biomarkers relative to the segmentation sets comprises:

first information, comprising information about the spatial distribution of biomarkers in a first one of the segmentation sets; and second information, comprising information about the spatial distribution of biomarkers in a second one of the segmentation sets, where the metric is generated using the first and second information for the first sample data unit and the first and second information for the second sample data unit, and wherein the generation of the metric comprises obtaining a vector having end points defined by the first and second information for the first sample data unit and the first and second information for the second sample data unit.

2. The method of claim 1, wherein the generation of the metric comprises calculating an argument or slope of the vector.

3. The method of claim 1, wherein the generation of the metric comprises calculating a magnitude of the vector.

4. The method of claim 1, wherein:

the generation of the metric comprises calculating an argument or slope of the vector and/or calculating a magnitude of the vector; and the method further comprises using the calculated arguments or slopes and/or magnitudes for plural different subjects, together with information about clinical efficacy and/or safety of an applied treatment, as input to a machine learning algorithm to build a predictive model.

5. The method of claim 1, further comprising generating a visual representation of the metric by displaying at least the end points of the vector on a graph.

6. The method of claim 5, wherein:

one axis of the graph represents a range of possible values of the first information; and the other axis of the graph represents a range of possible values of the second information.

7. The method of claim 1, wherein the information about the spatial distribution of biomarkers relative to the segmentation sets comprises information about a spatial density of the biomarkers in each of one or more of the segmentation sets.

8. The method of claim 7, wherein for at least one of the segmentation sets the segmentation set comprises plural regions of the image and the information about the spatial density of the biomarkers comprises region-specific information about the spatial density of the biomarkers in each of two or more of the regions.

9. The method of claim 8, wherein the generation of the metric comprises generating a metric representing a distribution of the spatial density of the biomarkers over the two or more of the regions, optionally in the form of a histogram.

10. The method of claim 1, wherein the plurality of segmentation sets comprises at least one segmentation set corresponding to tumor nest tissue.

11. The method of claim 1, wherein the plurality of segmentation sets comprises at least one segmentation set corresponding to a stroma tissue type.

12. The method of claim 1, wherein the biomarker comprises a stained cell.

13. The method of claim 1, wherein the biomarker comprises an immune cell, preferably a cytotoxic T cell.

14. The method of claim 1, wherein the segmented image in each sample data unit is obtained by applying a segmentation algorithm to an image of the respective biological sample taken from the subject.

15. The method of claim 1, wherein the treatment comprises application of an immunotherapy drug.

16. A computer program stored in a non-transitory computer-readable medium comprising instructions which, when the program is executed by a computer, cause the computer to carry out the method of claim 1.

17. A system comprising a processor and a non-transitory computer-readable medium for executing a computer program implementing the method of claim 1.

* * * * *